United States Patent
Fan et al.

(10) Patent No.: US 9,406,107 B2
(45) Date of Patent: Aug. 2, 2016

(54) SYSTEM AND METHOD OF COMPUTED TOMOGRAPHY SIGNAL RESTORATION VIA NOISE REDUCTION

(71) Applicant: General Electric Company, Schenectady, NY (US)

(72) Inventors: Jiahua Fan, Waukesha, WI (US); Meghan L. Yue, Waukesha, WI (US); Jiang Hsieh, Waukesha, WI (US); Roman Melnyk, Waukesha, WI (US); Masatake Nukui, Hino (JP); Yujiro Yazaki, Hino (JP)

(73) Assignee: GENERAL ELECTRIC COMPANY, Schenectady, NY (US)

(*) Notice: Subject to any disclaimer, the term of this patent is extended or adjusted under 35 U.S.C. 154(b) by 239 days.

(21) Appl. No.: 14/132,321

(22) Filed: Dec. 18, 2013

(65) Prior Publication Data

US 2015/0170341 A1    Jun. 18, 2015

(51) Int. Cl.
*G06T 5/00* (2006.01)
*A61B 6/03* (2006.01)
*G06T 11/00* (2006.01)
*A61B 6/00* (2006.01)

(52) U.S. Cl.
CPC . *G06T 5/002* (2013.01); *A61B 6/03* (2013.01); *A61B 6/5205* (2013.01); *A61B 6/5258* (2013.01); *G06T 11/005* (2013.01); *A61B 6/482* (2013.01); *A61B 6/582* (2013.01); *G01N 2223/401* (2013.01); *G01N 2223/419* (2013.01); *G06T 2207/10081* (2013.01); *G06T 2207/20182* (2013.01)

(58) Field of Classification Search
None
See application file for complete search history.

(56) References Cited

U.S. PATENT DOCUMENTS

| | | | |
|---|---|---|---|
| 8,588,494 B2 | 11/2013 | De Man et al. | |
| 2005/0249416 A1* | 11/2005 | Leue | G01V 5/005 382/195 |
| 2006/0029285 A1* | 2/2006 | Hein | G06T 5/50 382/260 |
| 2011/0286651 A1* | 11/2011 | Yu | G06T 11/005 382/131 |
| 2012/0106816 A1 | 5/2012 | De Man et al. | |
| 2012/0321157 A1* | 12/2012 | Yang | G06T 11/008 382/131 |
| 2013/0003914 A1 | 1/2013 | Yin et al. | |
| 2013/0089252 A1* | 4/2013 | Shechter | G06T 5/002 382/131 |
| 2013/0266115 A1 | 10/2013 | Fan et al. | |

* cited by examiner

*Primary Examiner* — Utpal Shah
*Assistant Examiner* — Mai Tran
(74) *Attorney, Agent, or Firm* — Fletcher Yoder, P.C.

(57) ABSTRACT

An imaging system includes a computer programmed to estimate noise in computed tomography (CT) imaging data, correlate the noise estimation with neighboring CT imaging data to generate a weighting estimation based on the correlation, de-noise the CT imaging data based on the noise estimation and on the weighting, and reconstruct an image using the de-noised CT imaging data.

17 Claims, 7 Drawing Sheets

SYSTEM AND METHOD OF COMPUTED TOMOGRAPHY SIGNAL RESTORATION VIA NOISE REDUCTION

BACKGROUND

This disclosure relates generally to diagnostic imaging and, more particularly, to an apparatus and method of restoring signals in computed tomography (CT) imaging system via noise reduction.

Typically, in computed tomography (CT) imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of x-ray detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the subject within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent to the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are transmitted to the data processing system for image reconstruction. Imaging data may be obtained using x-rays that are generated at a single polychromatic energy. However, some systems may obtain multi-energy images that provide additional information for generating images.

During scanning to acquire projection data, it is generally desirable to reduce x-ray dose received by the subject, thus protocols have been developed that reduce x-ray tube power and patient exposure during image data acquisition. Also, gantry speeds in CT imaging generally continue to increase over time, in an effort to capture images in a shorter time period to reduce motion artifacts. Thus, as dose is reduced and as gantry speed increases, the general trend is to reconstruct images using lower amounts of photons passing through the image volume, resulting in a reduced signal-to-noise ratio (SNR). As such, the effect of statistical noise has thereby increased, resulting in an increased propensity for noise-induced artifacts. Thus, there is a need to account for statistical noise in CT scanners.

To account for noise, signal restoration has traditionally been performed using closed-form or iterative solutions that are essentially based on neighbor pixels. For instance, in a known closed-form solution, signal restoration is performed through a weighted average of its neighbor pixels, using linear or non-linear noise filtering or smoothing algorithms such as Gaussian smoothing, bi-lateral filtering, and the like. In a known iterative solution, noise is estimated using an iterative "cost-optimization" approach in which the noise is iteratively estimated based on the surrounding pixels.

A disadvantage of such methods, however, is that while noise is averaged out, the contrast among neighboring pixels is also averaged out. Thus, when these known methods are applied to signals having a low SNR, a blurred version of the original signal can result.

Therefore, it would be desirable to improve the estimate of statistical noise without blurring the original signal.

BRIEF DESCRIPTION

Embodiments are directed toward a method and apparatus of de-noising and restoring signals in a computed tomography (CT) system in medical imaging.

According to one aspect, an imaging system includes a computer programmed to estimate noise in computed tomography (CT) imaging data, correlate the noise estimation with neighboring CT imaging data to generate a weighting estimation based on the correlation, de-noise the CT imaging data based on the estimation and on the weighting, and reconstruct an image using the de-noised CT imaging data.

According to another aspect, a method of imaging data processing includes estimating noise in computed tomography (CT) imaging data, correlating the noise estimation with neighboring CT imaging data, generating a weighting estimation based on the correlation, de-noising the CT imaging data based on the estimated noise and on the weighting estimation, and reconstructing an image using the de-noised CT imaging data.

According to yet another aspect, a non-transitory computer readable storage medium having stored thereon a computer program comprising instructions, which, when executed by a computer, cause the computer to estimate noise in computed tomography (CT) imaging data, correlate the noise estimation with neighboring CT imaging data to generate a weighting estimation based on the correlation, de-noise the CT imaging data based on the estimation and on the weighting, and reconstruct an image using the de-noised CT imaging data.

Various other features and advantages will be made apparent from the following detailed description and the drawings.

DETAILED DESCRIPTION

The operating environment of disclosed embodiments is described with respect to a sixty-four-slice computed tomography (CT) system. However, it will be appreciated by those skilled in the art that disclosed embodiments are equally applicable for use with other multi-slice configurations, or other imaging systems in general, such as an x-ray system on a c-arm or a micro-CT system, as examples. Moreover, disclosed embodiments will be described with respect to the detection and conversion of x-rays. However, one skilled in the art will further appreciate that embodiments are equally applicable for the detection and conversion of other high frequency electromagnetic energy. Disclosed embodiments will be described with respect to a "third generation" CT scanner, but is equally applicable with other CT systems as well as vascular and surgical C-arm systems and other x-ray tomography systems.

Figure 1:
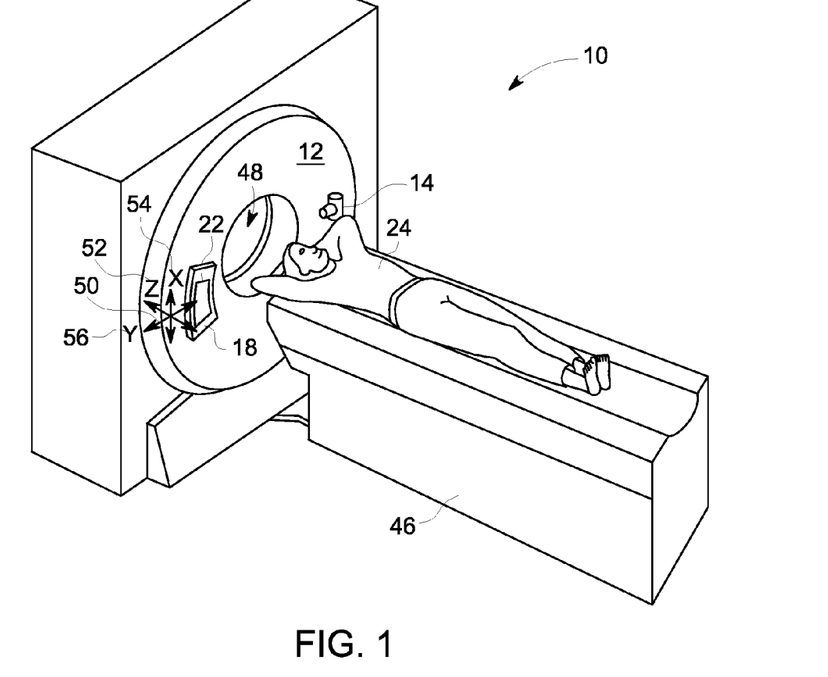
FIG. 1 is a pictorial view of a CT imaging system.
Figure 2:
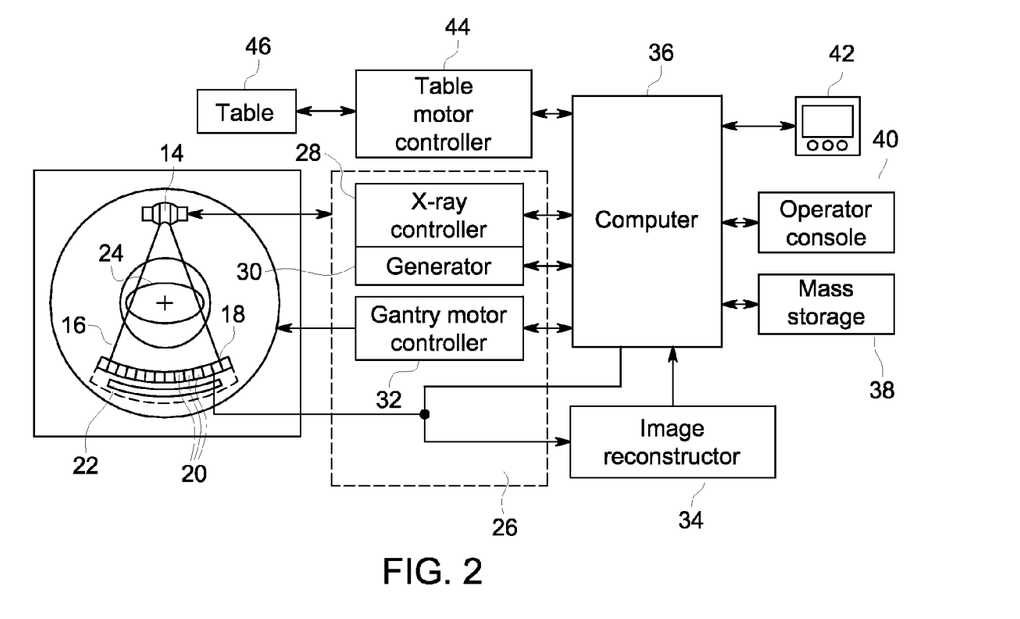
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. X-ray source 14 includes either a stationary target or a rotating target. Detector assembly 18 is formed by a plurality of detectors 20 and data acquisition systems (DAS) 22. The plurality of detectors 20 sense the projected x-rays that pass through a patient 24, and DAS 22 converts the data to digital signals for subsequent processing. Each detector 20 produces an analog electrical signal that represents the intensity of an impinging x-ray beam and hence the attenuated beam as it passes through patient 24. During a scan to acquire x-ray projection data, gantry 12 and the components mounted thereon rotate about a center of rotation.

Rotation of gantry 12 and the operation of x-ray source 14 are governed by a control mechanism 26 of CT system 10. Control mechanism 26 includes an x-ray controller 28 and generator 30 that provides power and timing signals to x-ray source 14 and a gantry motor controller 32 that controls the rotational speed and position of gantry 12. An image reconstructor 34 receives sampled and digitized x-ray data from DAS 22 and performs high speed image reconstruction. The reconstructed image is applied as an input to a computer 36 which stores the image in a mass storage device 38.

Computer 36 also receives commands and scanning parameters from an operator via an operator console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position patient 24 and gantry 12. Particularly, table 46 moves patients 24 through a gantry opening 48 in whole or in part. A coordinate system 50 for detector assembly 18 defines a patient or Z-axis 52 along which patient 24 is moved in and out of opening 48, a gantry circumferential or X-axis 54 along which detector assembly 18 passes, and a Y-axis 56 that passes along a direction from a focal spot of x-ray source 14 to detector assembly 18.

X-ray source 14, in accordance with present embodiments, is configured to emit x-ray beam 16 at one or more energies. For example, x-ray source 14 may be configured to switch between relatively low energy polychromatic emission spectra (e.g., at approximately 80 kVp) and relatively high energy polychromatic emission spectra (e.g., at approximately 140 kVp). As will be appreciated, x-ray source 14 may also be operated so as to emit x-rays at more than two different energies. Similarly, x-ray source 14 may emit at polychromatic spectra localized around energy levels (i.e., kVp ranges) other than those listed herein (e.g., 100 kVP, 120 kVP, etc.). Selection of the respective energy levels for emission may be based, at least in part, on the anatomy being imaged.

In some embodiments x-ray controller 28 may be configured to selectively activate x-ray source 14 such that tubes or emitters at different locations within system 10 may be operated in synchrony with one another or independent of one another. In certain embodiments discussed herein, the x-ray controller 28 may be configured to provide fast-kVp switching of x-ray source 14 so as to rapidly switch source 14 to emit X-rays at the respective polychromatic energy spectra in succession during an image acquisition session. For example, in a dual-energy imaging context, x-ray controller 28 may operate x-ray source 14 so that x-ray source 14 alternately emits x-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, fast-kVp switching operation performed by x-ray controller 28 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

Techniques to obtain energy sensitive measurements include: (1) scan with two distinctive energy spectra and (2) detect photon energy according to energy deposition in the detector. Such measurements provide energy discrimination and material characterization, and may be used to generate reconstructed images using a base material decomposition (BMD) algorithm. A conventional BMD algorithm is based on the concept that, in an energy region for medical CT, the x-ray attenuation of any given material can be represented by a proper density mix of two materials with distinct x-ray attenuation properties, referred to as the base or basis materials. The BMD algorithm computes two CT images that represent the equivalent density of one of the base materials based on the measured projections at high and low x-ray photon energy spectra, respectively.

Thus, CT image data is obtained that may be from a single or a dual energy application. CT reconstruction is generally a two-step process. The patient is placed on the scanner and an x-ray beam is caused to rotate about the patient, either in a helical or an axial operation. Detectors measure the pattern of radiation (projection) transmitted through the patient. Image reconstruction from the projections is performed using a filtered backprojection (FBP).

Figure 3:
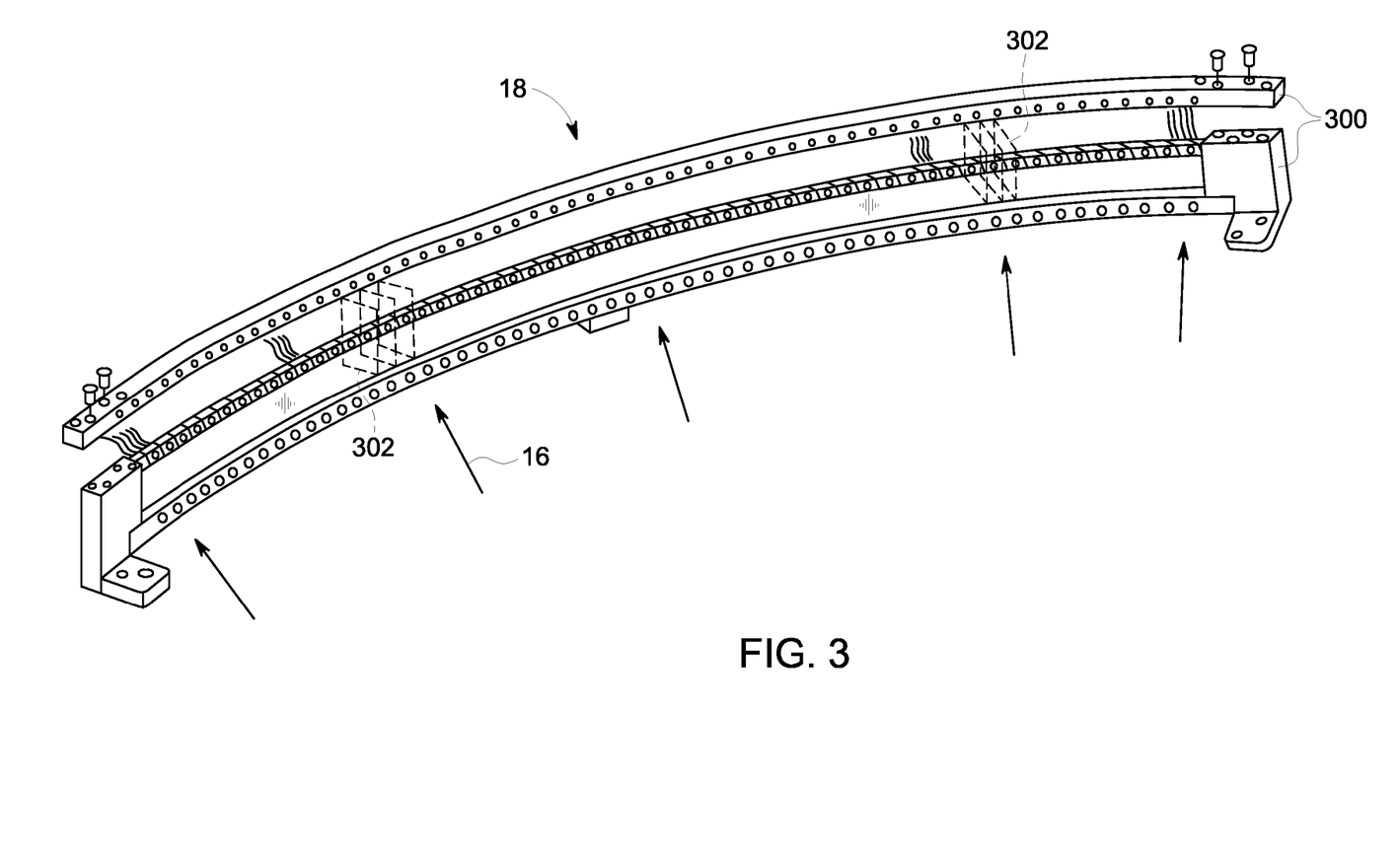
FIG. 3 is a perspective view of one embodiment of a CT system detector array.

As shown in FIG. 3, detector assembly 18 includes rails 300 having collimating blades or plates 302 placed therebetween. Plates 302 are positioned to collimate x-rays 16 before such beams impinge upon, for instance, detector 20 of FIG. 4 positioned on detector assembly 18. In one embodiment, detector assembly 18 includes fifty-seven detectors 20, each detector 20 having an array size of 64×16 of pixel elements 400. As a result, detector assembly 18 has sixty-four rows and nine hundred twelve columns (16×57 detectors) which allows sixty-four simultaneous slices of data to be collected with each rotation of gantry 12.

Figure 4:
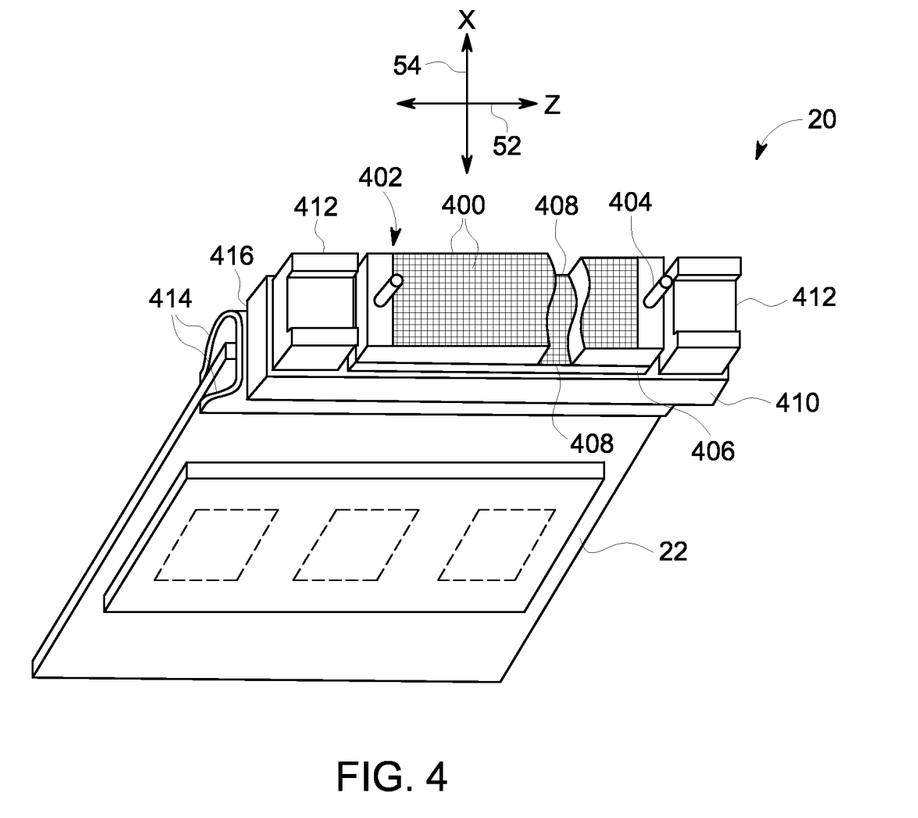
FIG. 4 is a perspective view of one embodiment of a detector.

Referring to FIG. 4, detector 20 includes DAS 22, with each detector 20 including a number of detector elements 400 arranged in pack 402. Detectors 20 include pins 404 positioned within pack 402 relative to detector elements 400. Pack 402 is positioned on a backlit diode array 406 having a plurality of diodes 408. Backlit diode array 406 is in turn positioned on multi-layer substrate 410. Spacers 412 are positioned on multi-layer substrate 410. Detector elements 400 are optically coupled to backlit diode array 406, and backlit diode array 406 is in turn electrically coupled to multi-layer substrate 410. Flex circuits 414 are attached to face 416 of multi-layer substrate 410 and to DAS 22. Detectors 20 are positioned within detector assembly 18 by use of pins 404.

Figure 5:
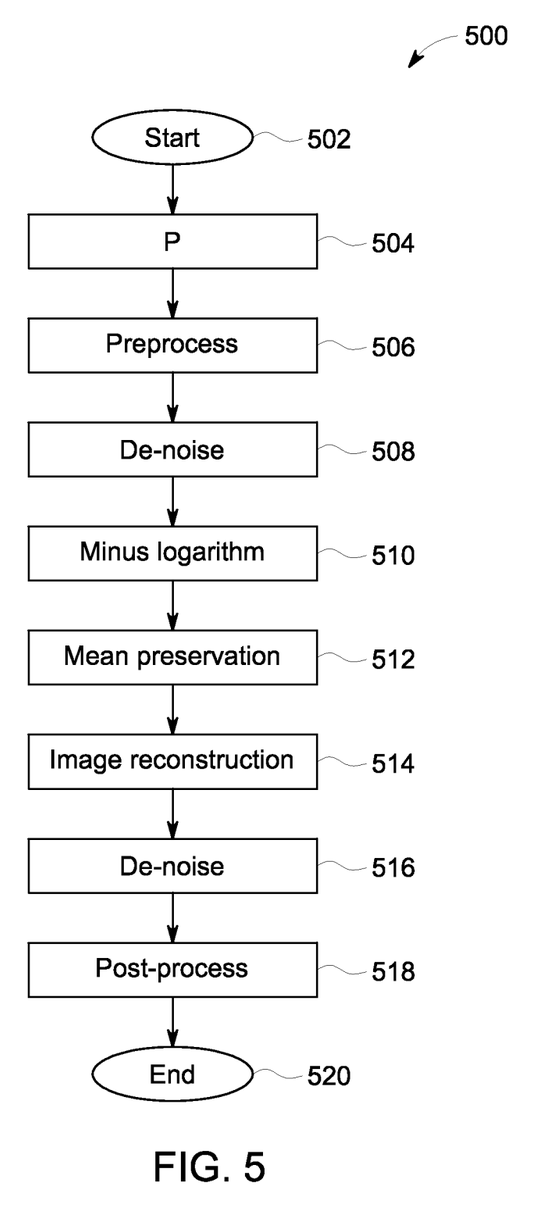
FIG. 5 is a process or flow diagram of a CT image formation process that incorporates the disclosed subject matter.

Referring to FIG. 5, a process or flow diagram 500 is illustrated of a CT image formation process that incorporates the disclosed subject matter. Starting at step 502, raw projection data is obtained at step 504 and preprocessed at step 506. Preprocessing step 506 includes but is not limited to such steps as source and detector calibration, accounting for patient-induced imperfections, and the like. At step 508, imaging data is de-noised in projection space, according to disclosed embodiments as will be further described. At step 510 and as commonly known, a "minus logarithm" step is applied in projection space which provides an integrated sum of attenuations of materials through which x-rays pass, resulting in a line integral along the path of respective x-rays. In one embodiment, at step 512 a mean preservation or correction is applied that accounts for a shift in the mean values that may occur as a result of the de-noising step 508. It is contemplated, in one embodiment, that an air calibration step is performed, typically at the end of the preprocessing step 506 and before the noise reduction step 508.

Image reconstruction occurs at step 514 which, in one embodiment, is a known tomographic reconstruction technique such as a filtered backprojection (FBP). However, it is contemplated that other image reconstruction techniques may be used as well. According to an embodiment of the disclosure, at step 516 imaging data is de-noised in image space, according to disclosed embodiments and as will be further described. At step 518, the images are post-processed, to include such steps as correcting for imaging artifacts. The process ends at step 520.

Figure 6:
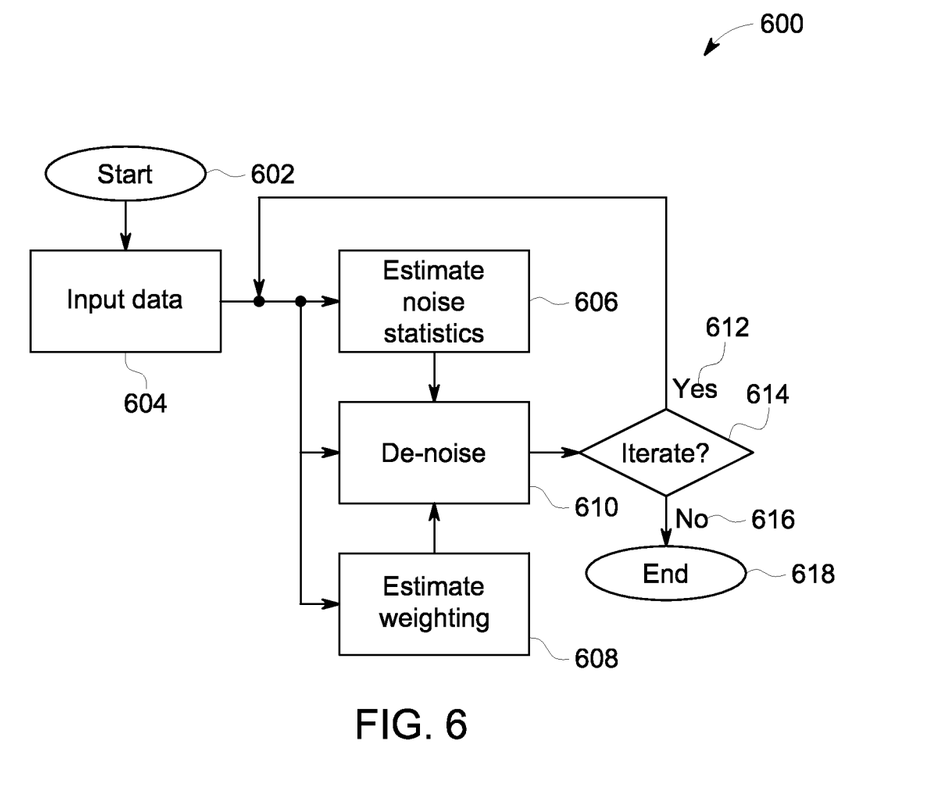
FIG. 6 illustrates a de-noising process that may be implemented in projection space or imaging space, and may be incorporated into the diagram of FIG. 5.

Referring to FIG. 6, CT imaging data is de-noised in either projection space (step 508) or in image space (516). A process or flow diagram 600 is illustrated having steps that may be applied in projection space, image space, or both, according to disclosed embodiments. Process 600 starts at step 602 in which input data at step 604 is obtained and noise is estimated at step 606, a weighting for the input data is estimated at step 608, and the input data is de-noised at step 610 based on the estimated noise statistics from step 606 and based on the estimated weighting at step 608. According to one embodiment, de-noising step 610 is performed without iteration, but in other embodiments, de-noising step 610 is iterated upon 612 by feeding the de-noised input data back into process 600, after which noise statistics are again estimated at step 606 and a weighting is again estimated at step 608, which are then used to iterate and produce a revised de-noise data at step 610. Process 600 may thereby include an iteration step 614 for one or more iterations, and when a threshold between iterations is reached, if no further iteration is performed 616, process 600 ends 618.

As such, according to one embodiment, process 600 includes one or more iterations that occur at block 614 until convergence occurs or a threshold is met. However, according to another embodiment, process 600 does not include an iteration option, thus in this example, at block 614 no iteration occurs 616 and the process ends 618.

Process 600 may be applied to de-noise imaging data in projection space (step 508) or in imaging space (516). Generally, therefore, an imaging system, such as imaging system 10 of FIG. 1, includes a computer 36 programmed to estimate noise in computed tomography (CT) imaging data, correlate the noise estimation with neighboring CT imaging data to generate a weighting estimation based on the correlation, de-noise the CT imaging data based on the estimation and on the weighting, and reconstruct an image using the de-noised CT imaging data. That is, whether in projection space or image space, steps 602-618 may be applied to the imaging data to reduce noise and improve the final image, with each step applicable to the particular space (projection or image). The de-noising update process to minimize a cost function can be carried out based on the following equation:

$$\frac{\partial y}{\partial t} = div[d(\|\nabla y\|) \cdot \nabla y];  \quad \text{Eqn. (1),}$$

where t represents the time sequence or the iteration, $\nabla$ is a gradient operator, and d is a monotonically decreasing function defined by:

$$d(z) = e^{-\frac{\eta z^2}{\sigma^2}}, \quad \text{Eqn. (2)}$$

where $\sigma$ is the data noise and $\eta$ is a parameter that controls the strength of the update. Noise, $\sigma$, is obtained through the accurate modeling of the noise statistics and is calculated for every measurement.

Projection Space

When in projection space and at step 508, the noise reduction process is conducted adaptively based on an estimation of noise behavior of each projection measurement. As such, when in projection space the input data at step 604 is projection data. Noise statistics are estimated at step 606, in one example, by estimating the variance of each measurement directly from the X-ray count using an approximate or assumed compound Poisson distribution. That is, and as commonly known, in this example a discrete probability distribution expresses the probability of a given number of events occurring in a fixed interval of time and/or space.

In order to do this, raw electron counts are converted back to x-ray counts. Note that, in an example using energy integration detectors, conversion factors can be experimentally determined for different energy spectra offered on the system. Signal-to-noise ratio (SNR) values are then formed for each measurement using the ratio of the measurement value over the noise standard deviation estimation. The SNR values estimated for each measurement may be used as the basis for the strength of the noise reduction for the measurement.

To facilitate the removal of the noise, estimation of a weighting at step 608 is based on at least one of a view, a channel, and a row of CT imaging data in projection space, and based on a correlation with a neighboring pixel or patch of pixels. That is, when in projection space, similarity information as it pertains to sinogram data is used to improve the estimation of the noise by taking advantage of the fact that noise may be correlated within the sinogram and for similar data therein. If a strong correlation is found, then larger weights can be applied at step 608. This similarity measurement could be implemented in the manner of pixels or patches. That is, one can simply compare the difference between two pixels or two patches centered at the two pixels. The differences will be grouped together to normalize and calculate the corresponding weights for similarity measure.

Note that for the sinogram process, the similarity measure should be computed after the negative log step 510 to ensure linearity of the measurement. At step 512, a mean preservation step is introduced to further ensure that the mean of the projection data is not shifted by the noise reduction process.

And, as summarized in FIG. 6, at block 614 the process may be iterated upon by cycling back through the steps to further decrease noise until convergence occurs, until a threshold difference of de-noised data is minimized, or for a fixed number of steps. The de-noising process is designed to compress noise while maintaining the signal, especially with respect to the edge of the signal. An edge preservation property is integrated in the process to ensure that the noise reduction is stopped when reaching an object edge, and resumes along the direction of the edge.

The neighboring pixels with a larger similarity measure and higher SNR will be weighted more in the process. Further, the de-noising process can use any type of edge and mean preserving noise reduction method. As has been discussed, the projection space de-noising is done based on direct noise estimation from the x-ray counts. The smaller the count, the larger the de-noising strength.

Image Space

When in image space and at step 508, (referring again to FIG. 6, but this time in the context of image space), the noise reduction process is conducted adaptively based on an estimation of noise behavior of image voxels. As such, when in image space the input data at step 604 is reconstructed image data. Noise statistics are estimated at step 606, in one example, by obtaining the image space noise statistic using the image space process.

To facilitate the removal of the noise, estimation of a weighting at step 608 is based on an estimation of a 3D image volume measure along pixels or patches of data. That is, when in image space, similarity information as it pertains to x-y-z voxel information, slice thickness, and the like, is used to improve the estimation of the noise by taking advantage of the fact that noise may be correlated within the image volume and for similar data therein. If a strong correlation is found, then larger weights can be applied at step 608. This similarity measurement could be implemented in the manner of pixels or patches. That is, one can simply compare the difference between two pixels or two patches centered at the two pixels. The differences will be grouped together to normalize and calculate the corresponding weights for similarity measure.

Figure 7A:
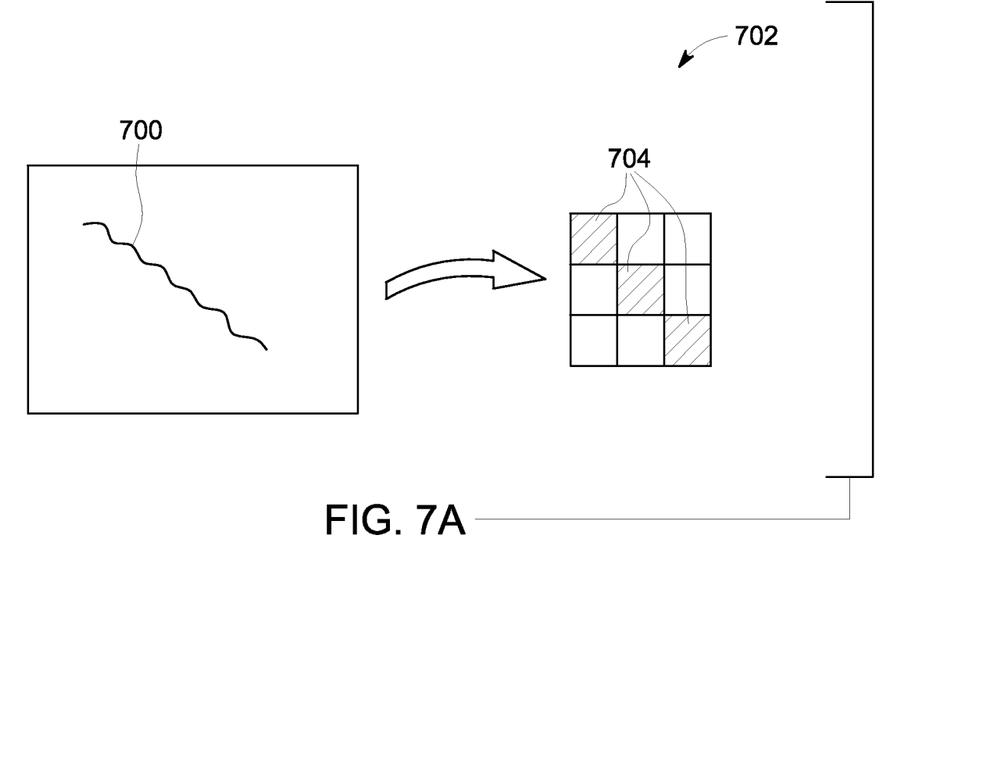
FIGS. 7A and 7B illustrate planar views that represent illustrative examples of statistics in image space that may be used to improve noise correlation.
Figure 7B:
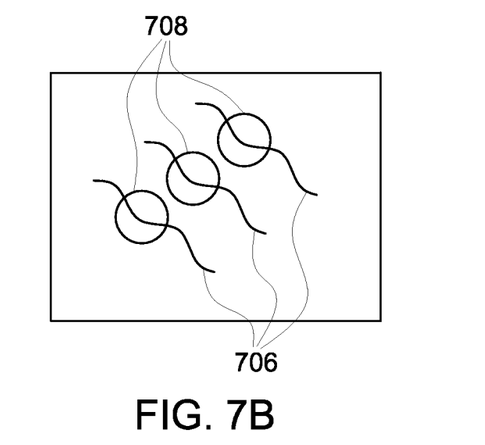

FIGS. 7A and 7B illustrate planar views that represent examples of statistics in image space that may be used to improve noise correlation. FIG. 7A, for instance, illustrates a wire 700 and a corresponding portion 702 of reconstructed imaging data in which pixels 704 correlate to wire 700. As such, the reconstruction computational complexity of pixels 704 are comparable with respect to each other, and given the knowledge that pixels 704 correspond to wire 700, it is contemplated that the weighting determined and applied at step 608 is thereby comparable to its neighboring pixel. FIG. 7B, as another example, includes three wires 706 having patches 708 that therefore also have comparable computational complexity and, given their approximate correlation to one another, may include similarity weighting at step 608 as well. Thus, in such examples, knowledge of the image can be used to augment the weighting based on pixel or patch similarity.

And, as summarized in FIG. 6, at block 614 the process may be iterated upon by cycling back through the steps to further decrease noise until convergence occurs, until a threshold difference of de-noised data is minimized, or for a fixed number of steps. The de-noising process is designed to compress noise while maintaining the signal, especially with respect to the edge of the signal. An edge preservation property is integrated in the process to ensure that the noise reduction is stopped when reaching an object edge, and resumes along the direction of the edge.

The neighboring pixels with a larger similarity measure and higher SNR will be weighted more in the process. Further, the de-noising process can use any type of edge and mean preserving noise reduction method. As has been discussed, the image space de-noising is done based on noise estimation from the image space process. The larger the noise estimation, the larger the de-noising strength.

The de-noising process can be done independently in projection (sinogram) space, as well as the image space, and can be done together and iteratively.

Figure 8:
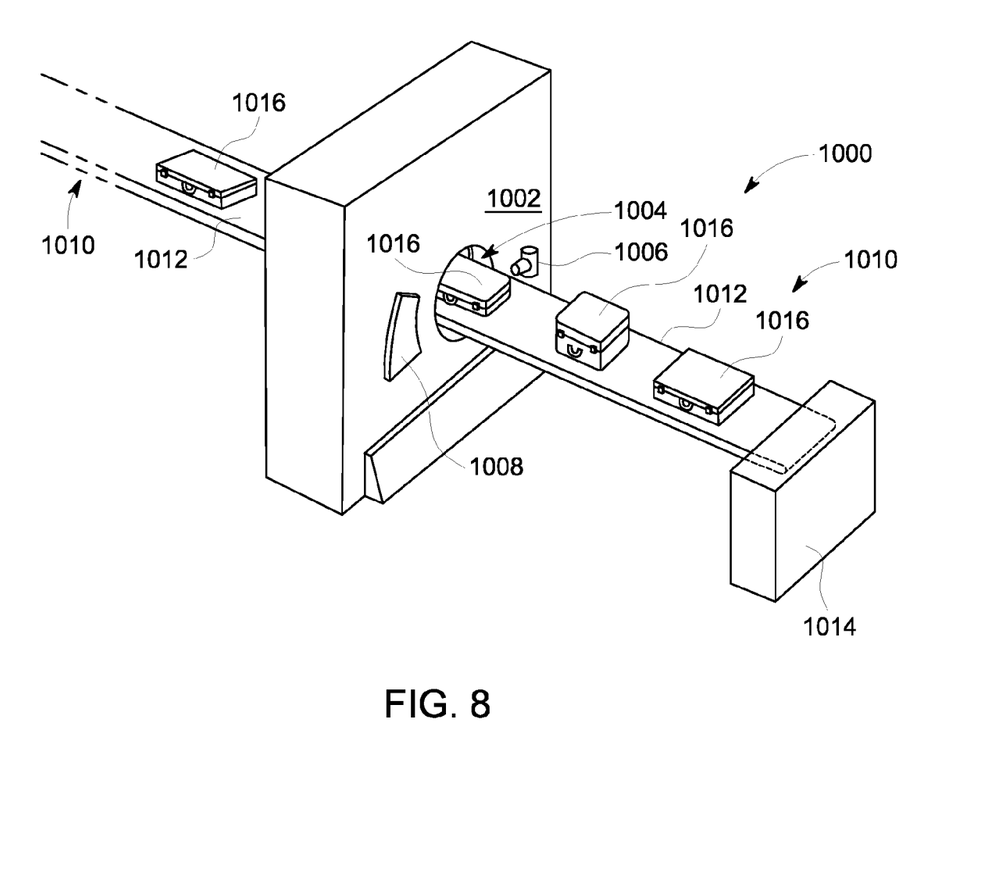
FIG. 8 is a pictorial view of a CT system for use with a non-invasive package inspection system.

Referring now to FIG. 8, there is shown a package/baggage inspection system 1000 that can use the image acquisition and reconstructions techniques according to embodiments disclosed and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of system 10 and/or 1000 in an example comprises a plurality of components such as one or more of electronic components, hardware components, and/or computer software components. A number of such components can be combined or divided in an implementation of the system 10 and/or 1000. An exemplary component of an implementation of the system 10 and/or 1000 employs and/or comprises a set and/or series of computer instructions written in or implemented with any of a number of programming languages, as will be appreciated by those skilled in the art. An implementation of system 10 and/or 1000 in an example comprises any (e.g., horizontal, oblique, or vertical) orientation, with the description and figures herein illustrating an exemplary orientation of an implementation of the system 10 and/or 1000, for explanatory purposes.

An implementation of system 10 and/or system 1000 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 1000 comprises the recordable data storage medium of the image reconstructor 34, and/or mass storage device 38 of computer 36. A computer-readable signal-bearing medium for an implementation of the system 10 and/or the system 1000 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 1000, for instance, one or more of a telephone network, a local area network ("LAN"), a wide area network ("WAN"), the Internet, and/or a wireless network.

According to one embodiment, an imaging system includes a computer programmed to estimate noise in computed tomography (CT) imaging data, correlate the noise estimation with neighboring CT imaging data to generate a weighting estimation based on the correlation, de-noise the CT imaging data based on the estimation and on the weighting, and reconstruct an image using the de-noised CT imaging data.

According to another embodiment, a method of imaging data processing includes estimating noise in computed tomography (CT) imaging data, correlating the noise estimation with neighboring CT imaging data, generating a weighting estimation based on the correlation, de-noising the CT imaging data based on the estimated noise and on the weighting estimation, and reconstructing an image using the de-noised CT imaging data.

According to yet another embodiment, a non-transitory computer readable storage medium having stored thereon a computer program comprising instructions, which, when executed by a computer, cause the computer to estimate noise in computed tomography (CT) imaging data, correlate the noise estimation with neighboring CT imaging data to generate a weighting estimation based on the correlation, de-noise the CT imaging data based on the noise estimation and on the weighting, and reconstruct an image using the de-noised CT imaging data.

A technical contribution for the disclosed method and apparatus is that it provides for a computer-implemented apparatus and method of de-noising and restoring signals in computed tomography (CT) image data.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Furthermore, while single energy and dual-energy techniques are discussed above, that disclosed encompasses approaches with more than two energies. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. An imaging system comprising a computer programmed to:
   perform an air calibration step on computed tomography (CT) imaging data, wherein the CT imaging data comprises projection measurement data;
   estimate noise in the projection measurement data;
   correlate the noise estimation with neighboring projection measurement data to generate a weighting estimation based on the correlation;
   de-noise the projection measurement data based on the noise estimation and on the weighting;
   calculate a negative logarithm of the projection measurement data;
   apply a mean preservation to the projection measurement data after calculating the negative logarithm; and
   reconstruct an image using the de-noised projection measurement data.

2. The imaging system of claim 1, wherein the computer is further programmed to estimate the noise based on a variance of each measurement using an x-ray count.

3. The imaging system of claim 2, wherein the computer is further programmed to estimate the variance based on an assumed Poisson distribution.

4. The imaging system of claim 2, wherein the computer is further programmed to correlate the noise estimation based on at least one of a view, a channel, and a row of CT imaging data in projection space.

5. The imaging system of claim 1, wherein after the image is reconstructed, the computer is further programmed to estimate noise in image space.

6. The imaging system of claim 1, wherein the computer is further programmed to correlate a noise estimate in a 3D image volume measured among one of a neighboring pixel or a neighboring patch of pixels.

7. The imaging system of claim 1, wherein the imaging system is a CT system that includes:
   a rotatable gantry for receiving an object to be scanned;
   a generator configured to energize an x-ray source to generate x-rays; and
   a detector positioned to receive the x-rays that pass through the object.

8. A method of imaging data processing, comprising:
   performing an air calibration step on computed tomography (CT) imaging data, wherein the CT imaging data comprises projection measurement data;
   estimating noise in the projection measurement data;
   correlating the noise estimation with neighboring projection measurement data;
   generating a weighting estimation based on the correlation;
   de-noising the projection measurement data based on the estimated noise and on the weighting estimation;
   calculating a negative logarithm of the projection measurement data;
   applying a mean preservation to the projection measurement data after calculating the negative logarithm; and
   reconstructing an image using the de-noised projection measurement data.

9. The method of claim 8, further comprising estimating the noise based on a variance of each measurement using an x-ray count.

10. The method of claim 9, further comprising estimating the variance based on an assumed Poisson distribution.

11. The method of claim 9, further comprising correlating the noise estimation based on at least one of a view, a channel, and a row of CT imaging data in projection space.

12. The method of claim 8, further comprising estimating a noise term after the image is reconstructed and in image space.

13. The method of claim 8, further comprising correlating a noise estimate in a 3D image volume measured among one of a neighboring pixel or a neighboring patch of pixels.

14. A non-transitory computer readable storage medium having stored thereon a computer program comprising instructions, which, when executed by a computer, cause the computer to:
  perform an air calibration step on computed tomography (CT) imaging data, wherein the CT imaging data comprises projection measurement data
  estimate noise in the projection measurement data;
  correlate the noise estimation with neighboring projection measurement data to generate a weighting estimation based on the correlation;
  de-noise the projection measurement data based on the estimation and on the weighting;
  calculate a negative logarithm of the projection measurement data;
  apply a mean preservation to the projection measurement data after calculating the negative logarithm; and
  reconstruct an image using the de-noised projection measurement data.

15. The non-transitory computer readable storage medium of claim 14, wherein the computer is further caused to estimate the noise based on a variance of each measurement using an x-ray count, and based on an assumed Poisson distribution.

16. The non-transitory computer readable storage medium of claim 14, wherein the computer is further programmed to estimate noise in image space.

17. The non-transitory computer readable storage medium of claim 14, wherein the computer is further caused to correlate a noise estimate in a 3D image volume measured among one of a neighboring pixel or a neighboring patch of pixels.

* * * * *